(12) United States Patent
Bellini et al.

(10) Patent No.: US 8,178,499 B2
(45) Date of Patent: May 15, 2012

(54) ESTER DERIVATIVES OF HYALURONIC ACID FOR THE PREPARATION OF HYDROGEL MATERIALS BY PHOTOCURING

(75) Inventors: Davide Bellini, Montegrotto Terme (IT); Anna Maria Zanellato, Bovolenta (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 664 days.

(21) Appl. No.: 12/246,805

(22) Filed: Oct. 7, 2008

(65) Prior Publication Data
US 2009/0075911 A1 Mar. 19, 2009

Related U.S. Application Data

(62) Division of application No. 10/507,472, filed as application No. PCT/EP03/02538 on Mar. 12, 2003, now Pat. No. 7,462,606.

(30) Foreign Application Priority Data

Mar. 12, 2002 (IT) .............................. PD2002A0064

(51) Int. Cl.
*A61K 31/7008* (2006.01)
*A61P 41/00* (2006.01)

(52) U.S. Cl. .......................................... 514/25; 536/53
(58) Field of Classification Search ................... 514/25; 536/53
See application file for complete search history.

(56) References Cited

U.S. PATENT DOCUMENTS

| | | | |
|---|---|---|---|
| 4,851,521 A | 7/1989 | della Valle et al. | |
| 5,410,016 A * | 4/1995 | Hubbell et al. | 528/354 |
| 5,573,934 A * | 11/1996 | Hubbell et al. | 435/177 |
| 6,027,741 A | 2/2000 | Cialdi et al. | |
| 6,031,017 A | 2/2000 | Waki et al. | |
| 6,258,870 B1 | 7/2001 | Hubbell et al. | |
| 7,462,606 B2 | 12/2008 | Bellini et al. | |
| 2009/0075911 A1 | 3/2009 | Bellini et al. | |

FOREIGN PATENT DOCUMENTS

| | | |
|---|---|---|
| EP | 0 138 572 B1 | 7/1990 |
| EP | 0 341 745 B1 | 12/1994 |
| EP | 0 749 982 A1 | 12/1996 |
| EP | 0 554 898 B1 | 5/1997 |
| EP | 1 095 064 | 2/2001 |
| EP | 0 971 961 B1 | 12/2002 |
| EP | 0 716 688 B1 | 9/2003 |
| IT | 1268954 | 3/1997 |
| WO | WO 95/24497 | 9/1995 |
| WO | WO 96/24392 | 8/1996 |
| WO | WO 96/37519 | 11/1996 |
| WO | WO 97/18244 | 5/1997 |
| WO | WO 00/01733 | 1/2000 |
| WO | WO 00/16818 | 3/2000 |

OTHER PUBLICATIONS

International Search Report for PCT/EP03/02538, completed Jun. 23, 2003, mailed Jul. 2, 2003.
U.S. Appl. No. 10/507,472, Prosecution Table of Contents, downloaded Jul. 23, 2010.
U.S. Appl. No. 10/507,472, Preliminary Amendment filed Sep. 10, 2004.
U.S. Appl. No. 10/507,472, Restriction Requirement dated Jan. 19, 2007.
U.S. Appl. No. 10/507,472, Reply to Restriction Requirement filed Feb. 16, 2007.
U.S. Appl. No. 10/507,472, Office Action dated Mar. 16, 2007.
U.S. Appl. No. 10/507,472, Reply to Office Action filed Jun. 18, 2007.
U.S. Appl. No. 10/507,472, Final Office Action dated Feb. 11, 2008.
U.S. Appl. No. 10/507,472, Reply to Final Office Action filed Mar. 13, 2008.
U.S. Appl. No. 10/507,472, Notice of Allowance and Notice of Allowability dated May 5, 2008.
U.S. Appl. No. 10/507,472, Reply to Notice of Allowance and Issue Fee Payment filed Jul. 31, 2008.
U.S. Appl. No. 10/507,472, Issue Notification dated Nov. 19, 2008.
U.S. Appl. No. 12/246,970, Prosecution Table of Contents, downloaded Jul. 23, 2010.
U.S. Appl. No. 12/246,970, Preliminary Amendment filed Oct. 7, 2008.
U.S. Appl. No. 12/246,970, Notice to File Corrected Application Papers and Notice Regarding Power of Attorney dated Nov. 4, 2008.
U.S. Appl. No. 12/246,970, Preliminary Amendment filed Nov. 13, 2008.
U.S. Appl. No. 12/246,970, Reply to Notice to File Corrected Application Papers and Notice Regarding Power of Attorney filed Nov. 26, 2008.
U.S. Appl. No. 12/246,970, Petition to Correct Filing Receipt filed Dec. 3, 2008.
U.S. Appl. No. 12/246,970, Notice of Acceptance of Power of Attorney dated Dec. 9, 2008.
Balazs et al., "Matrix Engineering," Blood Coagulation and Fibrinolysis 2:173-178, 1991.
Bignami et al., "The Extracellular Matrix of Rat Spinal Cord: A Comparative Study on the Localization of Hyaluronic Acid, Glial Hyaluronate-Binding Protein, and Chondroitin Sulfate Proteoglycan," Experimental Neurology 117:90-93, 1992.
Bilak et al., "Delayed Application of IGF-I and GDNF Can Rescue Already Injured Postnatal Motor Neurons," NeuroReport 12(11):2531-2535, 2001.
Bryant et al., "The Effects of Crosslinking Density on Cartilage Formation in Photocrosslinkable Hydrogels," Biomed. Sci. Instrum. 35:309-314, 1999.

(Continued)

*Primary Examiner* — Shaojia Anna Jiang
*Assistant Examiner* — Ganapathy Krishnan
(74) *Attorney, Agent, or Firm* — Clark & Elbing LLP

(57) ABSTRACT

The present invention relates to hyaluronic acid ester derivatives, whose carboxylic groups are partially esterified with hydroxy groups of propiophenone derivatives, to the hydrogel materials consisting of the said hyaluronic acid ester derivatives, to their preparation process by photocuring of the hyaluronic acid ester derivatives, and their use in the biomedical, sanitary and surgical fields, and in the medical field as controlled release systems for drugs.

17 Claims, 1 Drawing Sheet

OTHER PUBLICATIONS

Denizot et al., "Rapid Colorimetric Assay for Cell Growth and Survival-Modifications to the Tetrazolium Dye Procedure Giving Improved Sensitivity and Reliability," J. Immunol. Methods 89:271-277, 1986.

Fisher et al., "Synthesis and Properties of Photocross-Linked Poly(Propylene Fumarate) Scaffolds," J. Biomater. Sci. Polymer Edn. 12(6):673-687, 2001.

Goodman and Gilman's "The Pharmacological Basis of Therapeutics", 10$^{th}$ Ed., p. 54-57, 1996.

Holland et al., "Polymers for Biodegradable Medical Devices. 1. The Potential of Polyesters as Controlled Macromolecular Release Systems," J. Controlled Release 4:155-180, 1986.

Holly et al., "Wettability of Hydrogels I. Poly(2-Hydroxyethyl Methacrylate)," J. Biomed. Mater. Res. 9:315-326, 1975.

Lewis et al., "The Kinetics and Stereochemistry of the Decomposition of Secondary Alkyl Chlorosulfites," Am. Chem. Soc. 74:308-311, 1952.

Malmonge et al., "Biomechanical and Histological Evaluation of Hydrogel Implants in Articular Cartilage," Braz. J. Med. Biol. Res. 33(3):307-312, 2000.

Nguyen et al., "Photopolymerizable Hydrogels for Tissue Engineering Applications," Biomaterials 23:4307-4314, 2002.

Paige et al., "De Novo Cartilage Generation Using Calcium Alginate-Chondrocyte Constructs," Plastic and Reconstructive Surgery 97:179-180, 1996.

Perka et al., "Joint Cartilage Repair with Transplantation of Embryonic Chondrocytes Embedded in Collagen-Fibrin Matrices," Clinical and Experimental Rheumatology 18:13-22, 2000.

Sawhney et al., "Bioerodible Hydrogels Based on Photopolymerized Poly(ethylene glycol)-co-poly($\alpha$-hydroxy acid) Diacrylate Macromers," Macromolecules 26:581-587, 1993.

Siggia et al., "Quantitative Organic Analysis via Functional Groups," 4$^{th}$ ed., John Wiley and Sons Publications, 169-172, 1979.

Washington, D.C., U.S. Department of Health and Human Services, Public Health Service, Centers for Disease Control, National Institute of Occupational Safety and Healthy, "Registry of Toxic Effects of Chemical Substances," Doris V. Sweet editor, vol. 4, Edition 1985-1986:3911-3912.

* cited by examiner

ESTER DERIVATIVES OF HYALURONIC ACID FOR THE PREPARATION OF HYDROGEL MATERIALS BY PHOTOCURING

CROSS-REFERENCE TO RELATED APPLICATIONS

This application is a divisional of U.S. patent application Ser. No. 10/507,472, filed Sep. 10, 2004 now U.S. Pat. No. 7,462,606, which is a 371 of PCT/EP03/02538, filed on Mar. 12, 2003, which claims priority from Italian Patent Application No. PD2002A000064, filed on Mar. 12, 2002.

FIELD OF THE INVENTION

The present invention relates to hyaluronic acid ester derivatives and hydrogel materials consisting of said ester derivatives, their preparation process by photocuring, and their use in biomedical and surgical fields, as well as in the medical field as controlled release systems for drugs, thanks to their advantageous mechanical and viscoelastic properties.

STATE OF THE ART

Several gels and hydrogels are known, prepared starting from synthetic polymers such as poly-hydroxyethyl methacrylate (PHEMA) (Holly F. J. et al., *Biomed. Res.* 1975, 9: 315) or starting from semisynthetic derivatives of natural polysaccharides, such as the hyaluronic acid derivative cross-linked with vinyl sulphone (Balazs E. A. et al., *Blood Coagulation and Fibrinolysis*, 1991, 2: 173-178), which can be used in the prevention of adhesions, in the release of drugs or biologically active proteins and in the tissue repair processes.

For some years, hydrogels have been known to be used in surgery, where both non-resorbable polymers such as polyesters and polyamides and biodegradable polymers such as those based on collagen, glycolic acid and lactic acid (Holland, S. J. et al., *J. Controlled Release*, 1986, 4: 155-180) and hyaluronic acid are used. It is also known that hydrogels can be obtained by ultraviolet irradiation both from synthetic polymers (Amarpreet S. Sawhney et al., *Macromolecules*, 1993, 26: 581-587) and from semisynthetic derivatives such as hydrogels of cross-linked and polymerised macromers (U.S. Pat. No. 5,410,016), and that gels can be prepared from natural polymers such as hyaluronic acid (U.S. Pat. No. 6,031,017) or from various glycosamino glycans (European patent No. 0554898), thus obtaining hydrogel products useful for preventing extensive adhesions and for various biomedical applications such as drugs release.

The above said hydrogel materials are all obtained by cross-linking the polymer such as hyaluronic acid with photoreactive cross-linking agents such as divinylsulphone or other molecules all having at least a C=C bond.

Some of these cross-linking agents are toxic, and this obviously plays a role when the hydrogel is intended to apply for the use as biomedical material or similar uses. Moreover, with this type of cross-linking compounds, when the network structure of the hydrogel forms, low molecular weight compounds coming from irradiation of the above said cross-linking compounds are incorporated into the hydrogel structure, and are difficult to remove. Finally, the hyaluronic acid derivatives modified by the crosslinking with such compounds give rise to a gel which is not soluble in water or in aqueous solutions.

It is also known that gels useful for the encapsulation of biological material can be prepared starting from water-soluble biopolymers containing at least two unsaturation sites, by polymerisation with radicalic initiator solutions activated by radiation at a wavelength of between 320 and 900 nm (U.S. Pat. No. 6,258,870). The encapsulation of cells such as chondrocytes can be used to produce engineered cartilage (Bryant et al., *Biomed. Sci. Instrum.* 1999, 35: 309-314), while the photo-cross-linking of polymers with propylene-fumarate can lead to the formation of three-dimensional matrices for use in the reconstruction of bone tissue (Fisher J. P. et al., *J. Biomater. Sci. Polymer Ed.* 2001, 12 (6): 673-687).

Therefore, the need of novel hyaluronic acid derivatives useful for preparing hydrogels not showing the drawbacks mentioned above for the prior art materials, is deeply felt.

SUMMARY OF THE INVENTION

Now the Applicant has found that the specific ester derivatives of hyaluronic acid and of hyaluronic acid derivatives with the propiophenone derivatives of formula (I) reported hereinafter, when photocured, yield hydrogel material having advantageous mechanical and viscoelastic properties.

They are therefore subject of the present invention the ester derivatives of hyaluronic acid or of hyaluronic acid derivatives, wherein part of the carboxylic groups of hyaluronic acid or of hyaluronic acid derivatives is esterified with the propiophenone derivatives of formula (I)

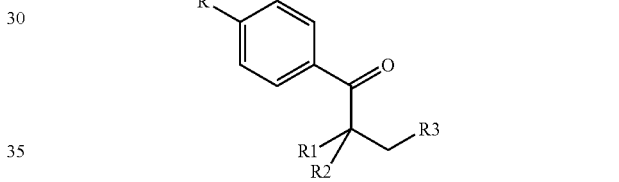

(I)

wherein R is selected from the group consisting of hydroxy, alkyloxy having an alkyl chain C1-C20 bearing one or more hydroxy groups, and heterocycle bearing one or more hydroxy groups;

and $R_1$, $R_2$ and $R_3$, equal or different amongst each other, are selected from the group consisting of hydrogen, hydroxy, alkyl C1-C20 possibly substituted with one or more hydroxy groups and alkyloxy C1-C20 possibly substituted with one or more hydroxy groups.

The preparation process of the present ester derivatives, as well as the hydrogel material consisting of the ester derivatives, the process for preparing the hydrogel material and the uses in biomedical and surgical fields, as well as in the medical field as controlled release systems for drugs, are further subjects of the present invention.

DETAILED DESCRIPTION OF THE INVENTION

Figure 1A:
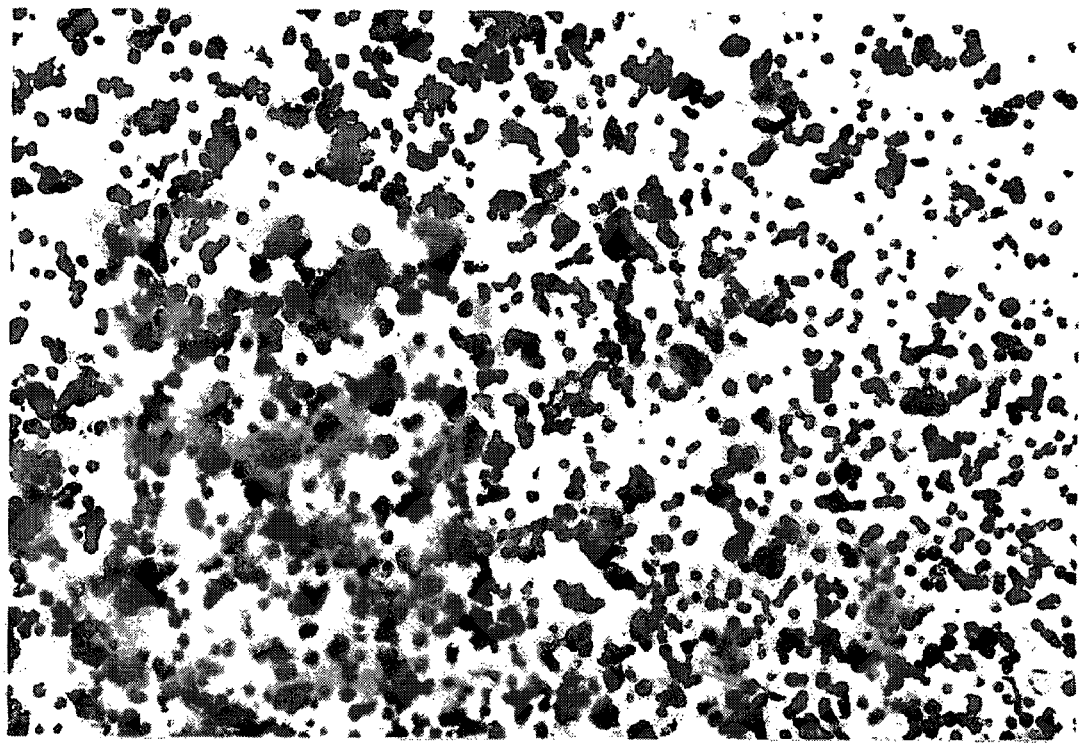
FIG. 1A: shows the stained viable cells magnified 10 times within the hydrogel of the invention after 24 hours in culture, prepared as in Example 10.

The ester derivatives of the invention may be prepared starting from molecules of hyaluronic acid or from derivatives thereof, such as those hereinafter reported, partially esterified with the propiophenone derivatives of formula (I) as radicalic initiators, capable of cross-linking without any C=C type unsaturation within the molecule.

The hyaluronic acid that can be used in the present invention may be obtained from any source, for example by extraction from rooster combs (European patent No. 0138572), or by fermentation (European patent application No. 0716688), or by biotechnology (Italian patent No. PD94A000042) and may have a molecular weight of between 400 and 3,000,000 Da, preferably of between 150,000 and 1,000,000 Da.

The starting hyaluronic acid derivatives of possible use according to the invention do not comprise C=C bonds, and are preferably selected from the group consisting of:

1) HYAFF®: hyaluronic acid esters with alcohols of the aliphatic, araliphatic, cycloaliphatic, aromatic, cyclic and heterocyclic series (as long as no double C=C bonds are present in said molecules), with a percentage of esterification that varies according to the type and length of the alcohol used, but never exceeds 75% so that the polymer remains water-soluble, while the remaining percentage of not esterified hyaluronic acid is salified with quaternary ammonium salts to enable a second esterification with the propiophenone derivatives of formula (I), like those disclosed in U.S. Pat. No. 4,851,521, we incorporate herewith by reference;

2) HYADD™: hyaluronic acid amides with amines of the aliphatic, araliphatic, cycloaliphatic, aromatic, cyclic and heterocyclic series (as long as no double C=C bonds are present in said molecules) with a percentage of amidation not exceeding 50% so that the polymer remains water-soluble, while the remaining percentage of hyaluronic acid which has not undergone amidation is salified with quaternary ammonium salts to enable a second esterification with the propiophenone derivatives of formula (I), like those disclosed in European patent application No. 1095064, we incorporate herewith by reference;

3) quaternary ammonium salts of O-sulphated derivatives like those disclosed in U.S. Pat. No. 6,027,741 we incorporate herewith by reference, or N-sulphated derivatives of hyaluronic acid like those disclosed in the European patent No. 0971961 we incorporate herewith by reference;

4) ACP®: inner esters of hyaluronic acid with a percentage of esterification not exceeding 20% so that the polymer remains water-soluble, while the remaining, non-esterified percentage of hyaluronic acid is salified with quaternary ammonium salts alone to enable a second esterification with the propiophenone derivatives of formula (I), like those disclosed in European patent No. 0341745 we incorporate herewith by reference.

Preferred propiophenone derivatives of formula (I) are selected from the group consisting of 4-(2,3-dihydroxypropoxy)-3-methoxy-propiophenone, 4'-(2-hydroxy-3-morpholinopropoxy)-propiophenone and 2-hydroxy-4-(2-hydroxyethoxy)-2-methyl-propiophenone (Register of Toxic Effect of Chemical Substance, 1985-86).

Particularly preferred is 2-hydroxy-4-(2-hydroxyethoxy)-2-methyl-propiophenone.

The present ester derivatives may be prepared by a process comprising the reaction of the starting hyaluronic acid or hyaluronic acid derivatives with the bromide of the propiophenone derivatives of formula (I), i.e. a compound of formula (I) wherein at least a hydroxy group of the substituent R is replaced by Br, to obtain the desired ester derivatives.

The bromides of the propiophenone derivatives of formula (I) can be prepared according to procedures well known to any person skilled in the art, such as according to the bromination reaction described by Lewis and Boozer in *Am. Chem. Soc.*, 1952, 74, 308.

In the present ester derivatives the percentage of carboxylic groups esterified with the above said propiophenone derivatives is preferably not exceeding 75%. The remaining carboxylic groups not esterified with the said propiophenone derivatives of formula (I) can be salified with quaternary ammonium salts or with alkaline or alkaline earth metals, preferably with sodium.

The present ester derivatives described above can be used for preparing new hydrogel materials based on hyaluronic acid that differ from all known gels and hydrogels based on hyaluronic acid, or containing other polymers together with hyaluronic acid. The present hydrogel materials consisting of the product obtained by photocuring the present ester derivatives optionally dissolved in water or in an aqueous solution. The photocuring may be carried out at a temperature ranging between 1 and 40° C., and preferably at room temperature.

When dissolved in water or in an aqueous solution, the concentration of the present ester derivatives may range for example between 0.01 and 100% (w/w), and preferably ranges between 0.1 and 50% (w/w).

The photocuring according to the invention is preferably carried out by irradiation with light having a wavelength ranging between 280 and 750 nm, and more preferably by irradiation with ultraviolet rays, and in particular with ultraviolet light having a wavelength of 366 nm.

The irradiation according to the invention is preferably carried out in an exposure time of between 2 and 30 minutes, and more preferably of between 3 and 15 minutes.

The thus obtained hydrogel materials show valuable properties, and in particular have the following characteristics:

a) absence of C=C unsaturation in the ester derivatives without the addition of any component acting as catalyst for the cross-linking reaction without any unsaturation within the molecule; until now, the presence of C=C unsaturation in the molecule to be cross-linked was thought to be indispensable for the radicalic initiator, and it was added either by chemical means or by simply mixing it with the polymer to be made into a gel, in order to trigger the polymerisation reaction;

b) sterility: it is possible to obtain a sterile hydrogel as the ester derivative is first steam-sterilised before photocuring;

c) excellent viscoelastic properties: the present hydrogel material is characterised by partial esterification with a radicalic initiator represented by a derivative of propiophenone and, moreover, by partial salification with quaternary ammonium salts or with alkaline or alkaline-earth metals. These hydrogels have a chemical-physical structure that is completely different from that of known gels constituted by inner or outer esters of hyaluronic acid. Indeed, the gels constituted by inner esters of hyaluronic acid are formed by microparticles of cross-linked polymer joined together by weak bonds of a physical kind. However, the outer esters can be in the form of a gel thanks to simple hydration, depending on the percentage of their esterification and their concentration in water. Conversely, the present hydrogel materials show a compact, wall-to-wall type, three-dimensional structure. They are therefore characterised by greater mechanical resistance (and can therefore be used to advantage in various sectors of medicine and surgery) and by viscoelastic properties that vary according to how long they have been exposed to irradiation and to the type of aqueous solution used to obtain the hydrogel. According to the invention redistilled water, buffers or normal saline, such as phosphate buffer or a salts solution, are preferably used to dissolve the present ester derivatives.

The present hydrogel materials thus prepared can be used to advantage in the biomedical, surgical, healthcare and pharmaceutical fields, and they may have many possible applications.

In particular biomaterials, healthcare products and surgical articles made of the present hydrogel materials can be prepared. The present hydrogel materials can be processed in the form of films, membranes and gauze pads, and can be used in dermatology to favour the wound-healing processes, in internal surgery to prevent superficial tissue adhesion, and as a polymer coating for organs and blood vessels.

Moreover, the present hydrogels may be useful in systems for the controlled release of one or more active ingredients such as proteins, growth factors, enzymes, anti-cancer drugs and steroid and non-steroid anti-inflammatory drugs, for topical, subcutaneous, intramuscular or intra-articular administration. In this last case, the use of the present hydrogel materials in the treatment of osteoarthritis as an alternative to the classic treatment for the condition is of particular interest. This therapy requires the intra-articular injection of steroid or non-steroid anti-inflammatory drugs and/or other "drugs" that have a mainly mechanical action of visco-supplementation.

The intra-articular injection of the present ester derivatives is also possible, with subsequent cross-linking by means of an endoscopic probe with optic fibres suitable for the in situ photocuring of the present ester derivatives and introduced into the knee by arthroscopy, enables the formation of a hydrogel material consisting of the present ester derivatives, directly into the synovial cavity. Said ester derivatives may be added with human fibroblasts and/or a drug, such as an anti-inflammatory drug and/or a metalloprotease inhibitor and/or a NO-synthase inhibitor or other biologically active molecules for use in the treatment of arthrosis and/or arthritis. When a drug is further added to the present ester derivatives, the hydrogel which forms in situ following to the irradiation allows the slow release of the drug, and simultaneously performs its mechanical action of visco-supplementation.

Moreover, hyaluronic acid in the form of a hydrogel has longer chemical degradation times than a visco-supplementation agent in fluid form. Indeed, in vitro tests performed to establish the degradation times of the present hydrogel without any incorporated drugs, showed that at 37° C. the hydrogel maintains its three-dimensional structure completely intact for as long as four weeks and more.

The scientific literature world-wide reports experiments performed with gels based on biocompatible but not biodegradable synthetic polymers (Malmonge et al., *Braz. J. Med. Biol. Res.* 2000, 33 (3): 307-312) surgically grafted into damaged joints as "artificial cartilage".

The hydrogel material of the invention differs substantially from the known polymers and from the above said type of graft because, besides being based on hyaluronic acid, known to be a highly biodegradable natural polymer that only releases non-toxic oligosaccharides, no arthrotomy is required for its application since the ester derivatives are injected in fluid form and cross-linked by means of an endoscopic probe suitable for photocuring the ester derivatives and introduced by arthroscopy.

A kit for implanting engineered cartilage by arthroscopic surgery is therefore a further subject of the invention, said kit comprising an ester derivative of the invention dissolved in water or in an aqueous solution, a container for the said ester derivative, preferably a container suitable for injection, and an endoscopic probe with optic fibres suitable for the in situ photocuring of the said ester derivative. The probe is preferably suitable for UV irradiation. The ester derivatives comprised in the present kit are preferably added by human fibroblasts and/or a drug, as above said.

Another subject of the present invention concerns the use of the present hydrogel materials in the processes of coating devices both in the medical field and in other sectors of industry, since they can endow the surfaces of the materials used as supports with new biological characteristics. The bio-coating constituted by the present hydrogel can also contain active ingredients such as drugs, proteins and growth factors that can be released from the polysaccharide matrix during application.

The devices that can be coated are, for example, selected from the group consisting of catheters, guide channels, cardiac valves, vascular stents, soft tissue prostheses, prostheses of animal origin such as porcine cardiac valves, artificial tendons, contact lenses and intraocular lenses, blood oxygenators, artificial organs such as kidneys, heart, liver and pancreas, blood bags, surgical instruments, filtration systems and laboratory instruments.

The process of coating the surfaces of said devices can be, for example, the Plasma Coating technique described in the international patent application by the Applicant, publication No. WO96/24392.

Another use of the present hydrogel material is the use for the controlled and continuous release of drugs, neuronal growth factors, antibodies, and association thereof, for the intramedullary administration, to favour regeneration of the bone marrow neurons especially after traumatic damages.

Indeed, it is known that some proteins such as IGF-I, GDNF and other neurotrophins can protect motor neurons from death when applied directly to the bone marrow lesion site by continuous infusion but they must be administered within a very limited time interval (Bilak M. M. et al., *Neuroreport* 2001, 8, 12 (11): 2531-35). It is also known that hyaluronic acid is present in the spinal cord, distributed both in the white matter, where it surrounds the myelin, and around the cell bodies of the neurons (Bignami A. et al., *Exp. Neurol.* 1992, 117 (1): 90-93).

Further subject of the present invention, the use of the present ester derivatives for the in situ administration, that is, directly into the damaged area of the bone marrow, of the aforementioned drugs mixed with the ester derivatives of the invention, which are first injected and then photopolymerised directly in the bone marrow. It is thus possible to obtain a continuous and controlled slow release of biologically and pharmacologically active ingredients without introducing any foreign and/or toxic product into the bone marrow, because, as already said above, hyaluronic acid is a natural component of the bone marrow substance.

This new type of intramedullar administration has been never described before, since all the drugs used in therapy for traumatised bone marrow are administered by continuous infusion directly into the lesion site.

The hydrogel material of the present invention may also be used for preparing scaffolds for the growth of numerous types of human or animal cells, both differentiated (such as keratinocytes, fibroblasts, osteocytes, adipocytes, chondrocytes) and not differentiated, such as mesenchymal stem cells of bone marrow.

The examples reported hereafter show that UV radiation does not alter the karyotype of the cells incorporated in the ester derivatives of the invention (that is polymerised) and that the viability and specific morphology of said cells remain unaltered. For this reason, it is possible to prepare in vitro and subsequently apply in vivo, various types of 'artificial tissue' especially of connective origin, constituted by cells incorporated in the hydrogel containing the factors necessary for their growth as well as their differentiation and cell function, such as epidermis, dermis, adipose tissue, bone tissue and cartilage tissue.

The cartilage tissue, described here as an example, represents a new type of engineered cartilage formed by a matrix constituted by the hydrogel containing differentiated cells (chondrocytes) or non-differentiated cells (stem cells) where the hyaluronic acid may be supplemented with growth factors and/or differentiating factors and/or other pharmacologically and/or biologically active ingredients, for the growth and differentiation of the cells it contains.

The construction thus prepared (hydrogel+cells) can be injected into the joint and subsequently cross-linked by irradiation thanks to a source of radiation introduced directly into the synovial cavity by arthroscopy. With this new type of engineered cartilage it is therefore possible to repair damaged cartilage by means of arthroscopy. The use of gels containing cells that are photopolymerised directly in the joint has never before been described. The world scientific literature on the topic only reports experiments performed with chondrocytes incorporated in collagen-fibrin gels (Perka et al., *Clin. Exp. Rheumatol.*, 2000, 18 (1): 13-22), or contained in alginate matrices (Paige K. T. et al., *Plas. Reconstr. Rug.* 1996, 97 (1): 179-180) or grown in agarose gels, surgically applied to the damaged cartilage, but in none of these experiments the gel containing the cells has been polymerised directly at the application site.

Another aim of the present invention concerns the use of hydrogels optionally with cells as viscoelastic substitutes for the nucleus pulposus of the intervertebral disk following degenerative pathologies or herniation of the spinal cord. Also in this case, the possibility of gelling the biopolymer by photo-cross-linking in situ by localised irradiation using endoscopic probes with optic fibres is very interesting and innovative.

Moreover, in relation to the particular viscoelastic characteristics of the hydrogels obtained by the photo-cross-linking of the present ester derivatives, they may be used in the field of ophthalmic surgery as visco-integrators of the vitreous humor. For purely descriptive purposes, without-limitation to the same, we report hereafter some examples of the preparation of hydrogels according to the present invention:

Example 1

Preparation of a Hyaluronic Acid Derivative with 70% of the Carboxylic Groups Esterified with 2-hydroxy-4-(2-hydroxyethoxy)-2-methylpropiophenone (HHMP) and the Remaining 30% of the Carboxylic Groups Salified with Sodium 6.21 g of tetrabutyl ammonium salt of hyaluronic acid, with a molecular weight of 180,000 Da (10 meq.) are solubilised in 248 ml of dimethylsulphoxide (DMSO) at room temperature. To this solution 2 g of HHMP bromide (7 meq) are added, and the so obtained solution is maintained at 37° C. for 48 hours. A 2.5% (w/w) solution of NaCl in water is then added and the resulting mixture is poured under stirring into 750 ml of acetone. A precipitate is formed which is then filtered and washed three times with 100 ml of a mixture acetone:water 5:1, then three times with 100 ml of acetone and lastly vacuum-dried for 24 hours at 30° C. 5.3 g of the product of the title is thus obtained. Quantitative determination of the content of HHMP is conducted by HPLC (high pressure liquid chromatography) after alkaline hydrolysis. The total content of ester groups is measured according to the saponification method described on pages 169-172 of "Quantitative organic analysis via functional group" fourth edition, John Wiley and Sons Publications.

Example 2

Preparation of a Hyaluronic Acid Derivative with 50% of the Carboxylic Groups Esterified with 2-hydroxy-4-(2-hydroxyethoxy)-2-methylpropiophenone (HHMP) and the Remaining 50% of the Carboxylic Groups Salified with Sodium 6.21 g of tetrabutyl ammonium salt of hyaluronic acid having a molecular weight of 180,000 Da (10 meq) are solubilised in 248 ml of DMSO at room temperature. To this solution 1.4 g of HHMP bromide (5 meq) are added, and the so obtained solution is maintained at 37° C. for 36 hours. A 2.5% (w/w) solution of NaCl in water is then added and the resulting mixture is poured under stirring into 750 ml of acetone. A precipitate is formed which is filtered and washed three times in 100 ml of the mixture acetone:water 5:1, then three times with 100 ml of acetone and finally vacuum dried for 24 hours at 30° C.

4.9 g of the desired product of the title is thus obtained. Quantitative determination of the HHMP content is performed by HPLC after alkaline hydrolysis. The total content of ester groups is measured according to the saponification method described on pages 169-172 of "Quantitative organic analysis via functional group" fourth edition, John Wiley and Sons Publications.

Example 3

Preparation of a Hyaluronic Acid Derivative with 25% of the Carboxylic Groups Esterified with 2-hydroxy-4-(2-hydroxyethoxy)-2-methylpropiophenone (HHMP) and the Remaining 75% of the Carboxylic Groups Salified with Sodium 6.21 g of tetrabutyl ammonium salt of hyaluronic acid having a molecular weight of 180,000 Da (10 meq) are solubilised in 248 ml of DMSO at room temperature. To this solution 0.72 g of HHMP bromide (2.5 meq) are added and the solution is maintained at 37° C. for 24 hours. A 2.5% (w/w) solution of NaCl in water is then added and the resulting mixture is poured into 750 ml of acetone under stirring. A precipitate is formed which is filtered and washed three times in 100 ml of the mixture acetone:water 5:1, then three times with 100 ml of acetone and finally vacuum dried for 24 hours at 30° C.

4.4 g of the desired product of the title are thus obtained. Quantitative determination of the HHMP content is performed by HPLC after alkaline hydrolysis. The total content of ester groups is measured according to the saponification method described on pages 169-172 of "Quantitative organic analysis via functional group" fourth edition, John Wiley and Sons Publications.

Example 4

Preparation of a Hyaluronic Acid Derivative with 0.25% of the Carboxylic Groups Esterified with 2-hydroxy-4-(2-hydroxyethoxy)-2-methylpropiophenone (HHMP), 25% of the Carboxylic Groups Esterified with Benzyl Alcohol and the Remaining 50% of the Carboxylic Groups Salified with Sodium 6.21 g of tetrabutyl ammonium salt of hyaluronic acid having a molecular weight of 180,000 Da (10 meq) are solubilised in 248 ml of DMSO at room temperature. To this solution 0.72 g of HHMP bromide (2.5 meq) are added and the solution is maintained at 37° C. for 24 hours. The solution is brought back to room temperature and supplemented with 0.29 ml of benzyl bromide (2.5 meq); it is then reheated to 37° C. for another 36 hours. A 2.5% (w/w) solution of NaCl in water is then added and the resulting mixture is poured into 750 ml of acetone under stirring. A precipitate is formed which is filtered and washed three times in 100 ml of the mixture acetone:water 5:1, then three times with 100 ml of acetone and finally vacuum dried for 24 hours at 30° C.

4.6 g of the desired product of the title are thus obtained. Quantitative determination of the content of HHMP and benzyl alcohol is performed by HPLC after alkaline hydrolysis. The total content of ester groups is measured according to the saponification method described on pages 169-172 of "Quantitative organic analysis via functional group" fourth edition, John Wiley and Sons Publications.

Example 5

Preparation of a Hyaluronic Acid Derivative with 15% of the Carboxylic Groups Amidated with Dodecyl Amine, 25% of the Carboxylic Groups Esterified with HHMP and the Remaining 60% of the Carboxylic Groups Salified with Sodium 6.21 g of tetrabutyl ammonium salt of hyaluronic acid having a molecular weight of 180,000 Da (10 meq) are solubilised in 248 ml of DMSO at room temperature. To this solution 0.6 ml (9 meq) are added with 99% methanesulphonic acid, and subsequently 0.240 g (1.5 meq) of 1,1'-carbonyldiimidazole (CDI). It is left to react at room temperature for 60-90 minutes. It is heated to 37° C. and 0.465 g (2.5 meq) of dodecyl amine are added. It is left to react for 24 hours at 37° C. The solution is allowed to go back to room temperature and 0.72 g of HHMP bromide (2.5 meq) are added. The solution is then reheated to 37° C. for 24 hours. A 2.5% (w/w) solution of NaCl in water is then added and the resulting mixture is poured under stirring into 750 ml of acetone. A precipitate is formed which is filtered and washed three times in 100 ml of the mixture acetone:water 5:1, then three times with 100 ml of acetone and finally vacuum dried for 24 hours at 30° C. 4.5 g of the desired product of the title are thus obtained. Quantitative determination of the content of HHMP and dodecyl amine is performed by HPLC after alkaline hydrolysis. The total content of ester groups is measured according to the saponification method described on pages 169-172 of "Quantitative organic analysis via functional group" fourth edition, John Wiley and Sons Publications.

Example 6

Preparation of a Hyaluronic Acid Ester with 50% of the Carboxylic Groups Esterified with HHMP and the Remaining 50% of the Carboxylic Groups Salified with Sodium, Starting from a Sulphated Hyaluronic Acid with a Degree of Sulphation of 3

Sulphation Degree=Number of OH Groups Replaced by $SO_3$ Groups in a Repeating Unit of Hyaluronic Acid 1 g of tetrabutyl ammonium salt of hyaluronic acid is solubilised in 40 ml of DMSO. To this solution 5.22 g of a $SO_3$-pyridine complex solubilised in 40 ml of DMSO are added. The solution is cooled to 4° C. and maintained under stirring for 1 hour. Subsequently, 200 ml of water are added and the pH of the final solution is adjusted to between 8.5 and 9.5 with a sodium hydroxide 1 M aqueous solution. By adding to the so obtained solution 850 ml of absolute ethanol, a precipitate is obtained, which is dialised to eliminate the residue salts. The so obtained product is solubilised in water and percolated on sulphonic resin in tetrabutyl ammonium form, thus yielding the initial salt. 12.7 g of sulphated hyaluronic acid having a degree of sulphation of 3 in the form of a tetrabutyl ammonium salt, are thus obtained.

7.9 g of the tetrabutyl ammonium salt of sulphated hyaluronic acid prepared as described above, with a molecular weight of 180,000 Da (5 meq), are solubilised in 248 ml of dimethylsulphoxide (DMSO) at room temperature. To this solution 0.7 g of HHMP bromide (2.5 meq) are added and the solution is maintained at 37° C. for 36 hours. A 2.5% solution (w/w) of NaCl in water is then added, and the resulting mixture is poured into 750 ml of acetone under stirring. A precipitate is formed which is filtered and washed three times in 100 ml of the mixture acetone:water 5:1, then washed three times with 100 ml of acetone and finally vacuum dried for 24 hours at 30° C. 4 g of the desired product of the title are thus obtained. Quantitative determination of the content of HHMP is performed by HPLC after alkaline hydrolysis. The total content of ester groups is measured according to the saponification method described on pages 169-172 of "Quantitative organic analysis-via functional group" fourth edition, John Wiley and Sons Publications.

Example 7

Preparation of a Hyaluronic Acid Derivative with 25% of the Carboxylic Groups Esterified with 2-hydroxy-4-(2-hydroxyethoxy)-2-methylpropiofenone (HHMP), 10% of the Carboxylic Groups Involved in the Formation of Inner Ester Bonds and the Remaining 65% of the Carboxylic Groups Salified with Sodium 6.21 g of tetrabutylammonium salt of hyaluronic acid with a molecular weight of 180,000 Da (10 meq) are solubilised in 248 ml of DMSO at room temperature. To this solution 0.72 g of HHMP bromide (2.5 meq) are added and the solution is maintained at 37° C. for 24 hours. Subsequently, 0.404 g of triethyl amine (4 meq) are added and the solution is stirred for 30 minutes. A solution of 1.022 g (4 meq) of 2-chloro-1-methyl-pyridine iodide in 100 ml of DMSO is added and the mixture is maintained at 30° C. for 15 hours. A 25% (w/w) solution of NaCl in water is added and the resulting mixture is poured into 750 ml of acetone under stirring. A precipitate is formed which is filtered and washed three times in 100 ml of the mixture acetone:water 5:1, then washed three times with 100 ml of acetone and, lastly, it is vacuum-dried for 24 hours at 30° C.

4.6 g of the desired product of the title are thus obtained. Quantitative determination of the content of HHMP and benzyl alcohol is performed by HPLC after alkaline hydrolysis. The total content of ester groups is measured according to the saponification method described on pages 169-172 of "Quantitative organic analysis via functional group" fourth edition, John Wiley and Sons Publications.

Example 8

Preparation of a Hydrogel from a Hyaluronic Acid Derivative with 70% of the Carboxylic Groups Esterified with 2-hydroxy-4-(2-hydroxyethoxy)-2-methylpropiophenone (HHMP) and the Remaining 30% of the Carboxylic Groups Salified with Sodium The ester derivative prepared as described above in Example 1 is solubilised at room temperature in purified water at a concentration of 25 g/l. The so obtained solution is exposed to ultraviolet radiation having a wavelength of 366 nm, using a UV lamp, CAMAG model (220 V; 0.18 A) for an exposure time of 30 minutes.

Example 9

Evaluation of the Effect of Ultraviolet (UV) Irradiation on the Karyotype of Irradiated Human Fibroblasts Three specimens of human fibroblasts ($2 \times 10^6$) are irradiated with UV light for three different times of exposure, for 3, 15 and 30 minutes.

After irradiation, each cell specimen is divided into two aliquots and treated as follows:
- the first aliquot is analysed immediately to determine the karyotype;
- the second aliquot is re-seeded in a culture dish containing 10% of foetal calf serum, hereinafter referred to as FCS, in Dulbecco's Modified Eagle Medium, hereinafter referred to as DMEM culture medium.

The second specimen of cells is left to proliferate for three cell cycles at the end of which the fibroblasts are prepared for determination of the karyotype.

Analyses performed on the cells immediately after irradiation and on the fibroblasts left in vitro for three life cycles, showed that no alterations occurred within the chromosomes during any of the periods of exposure to UV radiation.

Example 10

Culture of Human Fibroblasts Contained in the Hydrogel According to the Invention $2 \times 10^6$ fibroblasts are detached from the culture dish, centrifuged at 1500 rpm for 5 minutes and re-suspended in 3 ml of DMEM culture medium containing 10% of FCS. The cells are then added under gentle stirring to 3 ml of an aqueous solution of the hyaluronic acid derivative prepared as described above in Example 3 at a concentration of 100 mg/ml, giving a final solution of 6 ml containing $2 \times 10^6$ cells. This solution is re-seeded in culture wells, immediately irradiated with UV light for 12 minutes and then placed in an incubator set at 37° C. 24 hours later, the cells are MTT tested for cell viability: tetrazolium salt exposed to oxidation-reduction reaction only by mitochondrial enzymes of viable fibroblasts (Dezinot, F. et al., *J. Immunol. Methods*, 1986, 22 (89): 271-277).

Figure 1B:
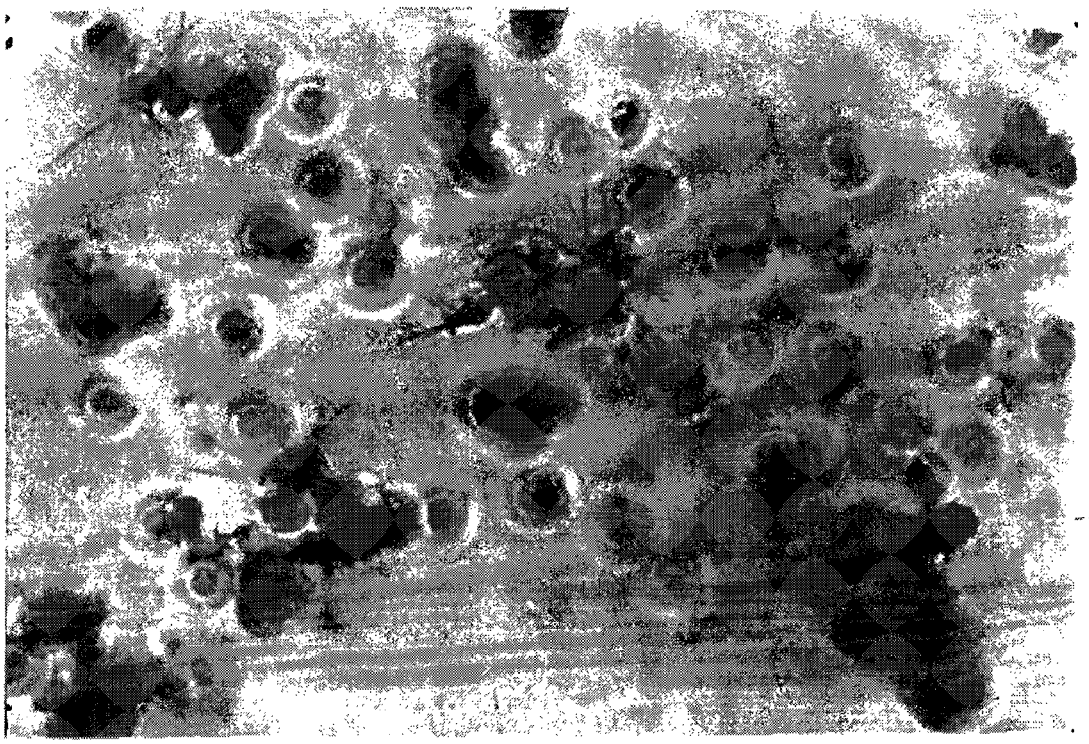
FIG. 1B shows the stained viable cells magnified 32 times within the hydrogel of the invention after 24 hours in culture, prepared as in Example 10.

FIGS. 1A and 1B show the stained viable cells (magnified 10 and 32 times respectively) within the present hydrogel after 24 hours in culture.

The invention being thus described, it is clear that these methods can be modified in various ways. Such modifications are not to be considered as divergences from the spirit and purpose of the invention and any modification that would be evident to an expert in the field comes within the scope of the following claims.

The invention claimed is:

1. Hydrogel consisting of a cross-linked product obtained by photocuring an aqueous solution of an ester derivative of hyaluronic acid or of hyaluronic acid derivatives, wherein part of the carboxylic groups of hyaluronic acid or of hyaluronic acid derivatives is esterified with the propiophenone derivatives of formula (I)

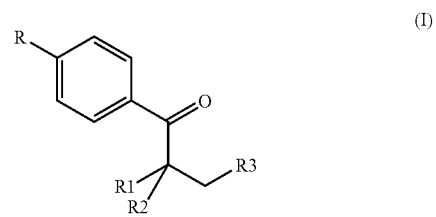

wherein R is selected from the group consisting of hydroxyl, alkyloxy having an alkyl chain C1-C20 bearing one or more hydroxyl groups, and heterocycle bearing one or more hydroxyl groups;

and $R_1$, $R_2$ and $R_3$, equal or different amongst each other, are selected from the group consisting of hydrogen, hydroxyl, alkyl C1-C20 possibly substituted with one or more hydroxyl groups and alkyloxy C1-C20 possibly substituted with one or more hydroxyl groups, wherein said ester is in a concentration between 0.01 and 100% (w/w).

2. Hydrogel according to claim 1, wherein the said photocuring is carried out by irradiation with light having a wavelength ranging between 280 and 750 nm.

3. Hydrogel according to claim 1, wherein the said photocuring is carried out by irradiation with ultraviolet rays.

4. Hydrogel according to claim 1, wherein the said photocuring is carried out by irradiation with light having a wavelength of 366 nm.

5. Hydrogel according to claim 1, wherein the concentration of the said ester derivatives ranges between 0.1 and 50% (w/w).

6. Hydrogel according to claim 1, wherein the said photocuring is carried out in an exposure time ranging between 2 and 30 minutes.

7. Hydrogel according to claim 6, wherein the said photocuring is carried out in an exposure time ranging between 3 and 15 minutes.

8. Hydrogel according to claim 1, wherein the said photocuring is carried out at a temperature ranging from 1 to 40° C.

9. Hydrogel according to claim 8, wherein the said photocuring is carried out at room temperature.

10. Biomedical materials, healthcare products and surgical articles selected from the group consisting of catheters, guide channels, cardiac valves, vascular stents, soft tissue prostheses, prostheses of animal origin, porcine heart valves, artificial tendons and organs, contact lenses and intra-ocular lenses, blood oxygenators, and blood bags, made of or coated by the hydrogel as claimed in claim 1.

11. Biomedical materials, healthcare products and surgical articles according to claim 10, coated by the hydrogel by of the plasma coating technique.

12. Scaffolds for the growth of human and animal, differentiated and/or undifferentiated cells comprising the hydrogel as claimed in claim 1.

13. Pharmaceutical composition comprising the hydrogel as claimed in claim 1.

14. Pharmaceutical composition according to claim 13, further comprising a pharmacologically and/or biologically active substance or an association thereof, said substance being a growth factor, antibody, anti-cancer drug, steroid anti-inflammatory drug, non-steroid anti-inflammatory drug, metalloprotease inhibitor, or NO-synthase inhibitor.

15. Pharmaceutical composition according to claim 13, for topical, subcutaneous, intramuscular, intra-articular and intra-medullar administration.

16. Pharmaceutical composition according to claim 14, wherein the hydrogel is the agent for controlled release of the active substances.

17. A method of prevention of post-surgical adhesions comprising treating a subject in need thereof with the hydrogel as claimed in claim 1.

* * * * *